United States Patent
Abe et al.

(10) Patent No.: US 6,540,669 B2
(45) Date of Patent: Apr. 1, 2003

(54) FLEXIBLE TUBE FOR AN ENDOSCOPE AND ELECTRONIC ENDOSCOPE EQUIPPED WITH THE FLEXIBLE TUBE

(75) Inventors: Masanao Abe, Saitama (JP); Shinji Hayakawa, Saitama (JP); Kikuo Iwasaka, Saitama (JP); Minoru Matsushita, Tokyo (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/942,720

(22) Filed: Aug. 31, 2001

(65) Prior Publication Data

US 2002/0045803 A1 Apr. 18, 2002

(30) Foreign Application Priority Data

Aug. 31, 2000 (JP) ........................................ 2000-264075

(51) Int. Cl.$^7$ ................................................ A61B 1/00
(52) U.S. Cl. ........................................ 600/140; 600/139
(58) Field of Search ........................ 600/139, 140, 600/121; 604/524, 526, 527

(56) References Cited

U.S. PATENT DOCUMENTS

| | | | | |
|---|---|---|---|---|
| 4,690,175 A | * | 9/1987 | Ouchi et al. | 600/140 |
| 4,753,222 A | * | 6/1988 | Morishita | 600/140 |
| 4,899,787 A | * | 2/1990 | Ouchi et al. | 600/140 |
| 5,217,002 A | * | 6/1993 | Katsurada et al. | 600/139 |
| 5,448,988 A | * | 9/1995 | Watanabe | 600/139 |
| 5,876,331 A | * | 3/1999 | Wu et al. | 600/139 |
| 5,885,207 A | * | 3/1999 | Iwasaka | 600/139 |
| 5,916,147 A | * | 6/1999 | Boury | 600/139 |
| 6,083,152 A | * | 7/2000 | Strong | 600/139 |
| 6,197,014 B1 | * | 3/2001 | Samson et al. | 604/524 |
| 6,206,824 B1 | * | 3/2001 | Ohara et al. | 600/139 |
| 6,402,687 B1 | * | 6/2002 | Ouchi | 600/139 |
| 6,458,075 B1 | * | 10/2002 | Sugiyama et al. | 600/139 |

FOREIGN PATENT DOCUMENTS

| | | |
|---|---|---|
| JP | 5-50287 | 7/1993 |
| JP | 10127572 | 5/1998 |

* cited by examiner

*Primary Examiner*—Linda C. M. Dvorak
*Assistant Examiner*—Jocelyn Ram
(74) *Attorney, Agent, or Firm*—Greenblum & Bernstein, P.L.C.

(57) ABSTRACT

An flexible tube for an endoscope having excellent resilience and durability is disclosed. The flexible tube is composed of a tubular core boy obtained by covering the outer periphery of a coil with a reticular tube of a braided thin wires and an outer cover formed of a synthetic resin and provided over the outer periphery of the tubular core boy. At least one of the thin wires has a coating layer and the flexible outer cover has a portion which is in contact with the coating layer of the thin wire of the reticular tube, in which the coating layer is formed of a material containing the material of the portion of the outer cover, and the material of the coating layer has a higher melting point than that of the material of the portion of the outer cover. The outer cover may be formed into a multi-layered structure including an inner layer, an intermediate layer and an outer layer.

12 Claims, 5 Drawing Sheets

FLEXIBLE TUBE FOR AN ENDOSCOPE AND ELECTRONIC ENDOSCOPE EQUIPPED WITH THE FLEXIBLE TUBE

BACKGROUND OF THE INVENTION

1. Field of the Invention

This invention relates to a flexible tube for an endoscope and an electronic endoscope equipped with the flexible tube.

2. Description of the Prior Art

Generally, a flexible tube for an endoscope has a structure which includes a tubular core obtained by covering the outer periphery of a helical coil with a reticular tube (braided tube) and an outer cover formed of a synthetic resin or the like and provided over the outer periphery of the tubular core.

In endoscopic examination, the flexible tube for an endoscope is inserted along the body cavity to a deep part such as the stomach, duodenum, small intestine, and large intestine with being bent appropriately according to the shape of the path. In order to perform the inserting operation easily and reliably, it is necessary for the flexible tube that a push-in force applied to the proximal end (an end which is close to the operator) of the flexible tube is fully transmitted to its distal end. However, if bucking occurs in the flexible tube, the push-in force can not be fully transmitted to the distal end because the push-in force is partially absorbed by the bent part where the buckling occurs. This means that such a flexible tube for an endoscope can not achieve reliable inserting operation. In order to avoid the occurrence of such buckling, it is necessary for the flexible tube to have sufficient flexibility so that such buckling is hard to occur. Further, the outer cover must be firmly attached or bonded to the tubular core since buckling is liable to occur at areas where the outer cover is peeled off from the tubular core.

Furthermore, in order to perform the inserting operation easily and reliably, it is also necessary for the flexible tube that when a rotational force (a twist) is applied to the proximal end thereof, the rotation is fully transmitted to the distal end thereof without being absorbed somewhere along the flexible tube. In other word, a flexible tube for an endoscope is also required to have satisfactory rotation followability at the distal end thereof for rotational force applied at the proximal end.

One example of such flexible tubes is disclosed in Japanese Examined Patent Publication No. Hei 5-50287, in which an outer cover of a flexible tube for an endoscope is constructed from a double layer structure composed of an outer layer made of a material having good flexibility and an inner layer made of a material having good resiliency, thereby improving resiliency of the flexible tube for an endoscope as a whole.

However, in the above-mentioned prior art, the adhesion (bonding strength) between the outer cover and the core has been left out of consideration. Therefore, in the flexible tube of the prior art, there is a case that the outer cover is peeled off from the core by repeated use thereof and thereby buckling is liable to occur and the resiliency of the flexible tube is lowered. In other words, the prior art flexible tube involves a problem in its durability.

SUMMARY OF THE INVENTION

It is therefore an object of the present invention to provide a flexible tube for an endoscope which has excellent resiliency and durability.

In order to achieve the above object, the present invention is directed to a flexible tube for an endoscope which comprises an elongated core body composed of a helical coil member which is formed by helically winding a flat band member and a braided member formed by braiding thin wires and provided over the coil; and a flexible outer cover for covering the core body. In the flexible tube, at least one of the thin wires has a coating layer and the flexible outer cover has a portion which is in contact with the coating layer of the thin wire of the braided member, in which the coating layer is formed of a material containing the material of the portion of the outer cover, and the material of the coating layer has a higher melting point than that of the material of the portion of the outer cover.

As described above, by forming such a coating layer on at least one of the fine wires, the present invention makes it possible to improve the adhesion between the braided member (reticular tube) and the outer cover. As a result, the present invention makes it possible to obtain a flexible tube for an endoscope having excellent resilience and durability. Further, it is also possible to prevent the coating layer from being melted when the outer cover is formed.

In a preferred embodiment, the coating layer contains a material that is the same as the material of the portion of the outer cover in the amount of 5 to 80 wt % thereof.

Further, in the preferred embodiment, the outer cover is formed of a material containing polyurethane based elastomer. This makes it possible to obtain a flexible tube for an endoscope having excellent flexibility.

Furthermore, in the preferred embodiment the coating layer is formed of a material containing polyurethane based elastomer. When such a material containing the polyurethane-based elastomer is employed as the constituent material of the coating layer 231, it is also possible to obtain excellent adhesion between the outer cover 3 and the coating layer 231 and it is also possible for the flexible tube 1 to have excellent flexibility in the case where the constituent material of the outer cover 3 is polyurethane-based elastomer (in particular, a material containing polyurethane-based elastomer as its main ingredient).

Moreover, in the preferred embodiment, the coating layer is formed of a material containing polyamide based elastomer. When the constituent material of the coating layer contains polyamide-based resin, it is possible to obtain excellent adhesion between the coating layer and the fine wires and excellent adhesion between the coating layer and the outer cover. This also improves the adhesion between the reticular tube and the outer cover, and as a result, the flexible tube will have excellent resilience and durability.

Moreover, in the preferred embodiment, the difference between the melting point of the material of the coating layer and the melting point of the material of the portion of the outer cover is in the range of 4 to 200° C.

In the present invention, it is preferred that the average thickness of the coating layer is in the range of 0.01 to 0.1 mm.

Further, it is also preferred that the average thickness of the outer cover is in the range of 0.01 to 1.5 mm.

Furthermore, it is also preferred that the outer cover is formed by extrusion molding.

In another preferred embodiment of the present invention, the outer cover is formed into a laminated structure including an inner layer, an intermediate layer and an outer layer, and the inner layer is formed of a material that exhibits adhesion with the coated layer. This makes it possible to provide a narrow flexible tube for an endoscope.

Another aspect of the present invention is directed to an electronic endoscope, comprising an operation section which is operated by an operator; and a flexible tube having a proximal end connected to the operation section at the proximal end thereof, the flexible tube including an elongated tubular core composed of a helical tubular member which is formed by helically winding a flat band member and a braided member formed by braiding thin wires and an a flexible outer cover formed of a synthetic resin and provided over the outer periphery of the tubular core, wherein at least one of the thin wires has a coating layer and the flexible outer cover has a portion which is in contact with the coating layer of the thin wire of the braided member, in which the coating layer is formed of a material containing the material of the portion of the outer cover and the material of the coating layer has a higher melting point than that of the material of the portion of the outer cover.

Further, in a preferred embodiment, the outer cover is formed into a laminated structure including an inner layer, an intermediate layer and an outer layer, and the inner layer is formed of a material that exhibits adhesion with the coated layer. This makes it possible to provide an arrow flexible tube for an endoscope.

These and other objects, structures and results of the present invention will be apparent more clearly when the following detailed description of the preferred embodiments is considered taken in conjunction with the accompanying drawings.

DETAILED DESCRIPTION OF THE INVENTION

Hereinafter, detailed description of the preferred embodiments of a flexible tube for an endoscope according to the present invention will be given with reference to the appended drawings.

Figure 1:
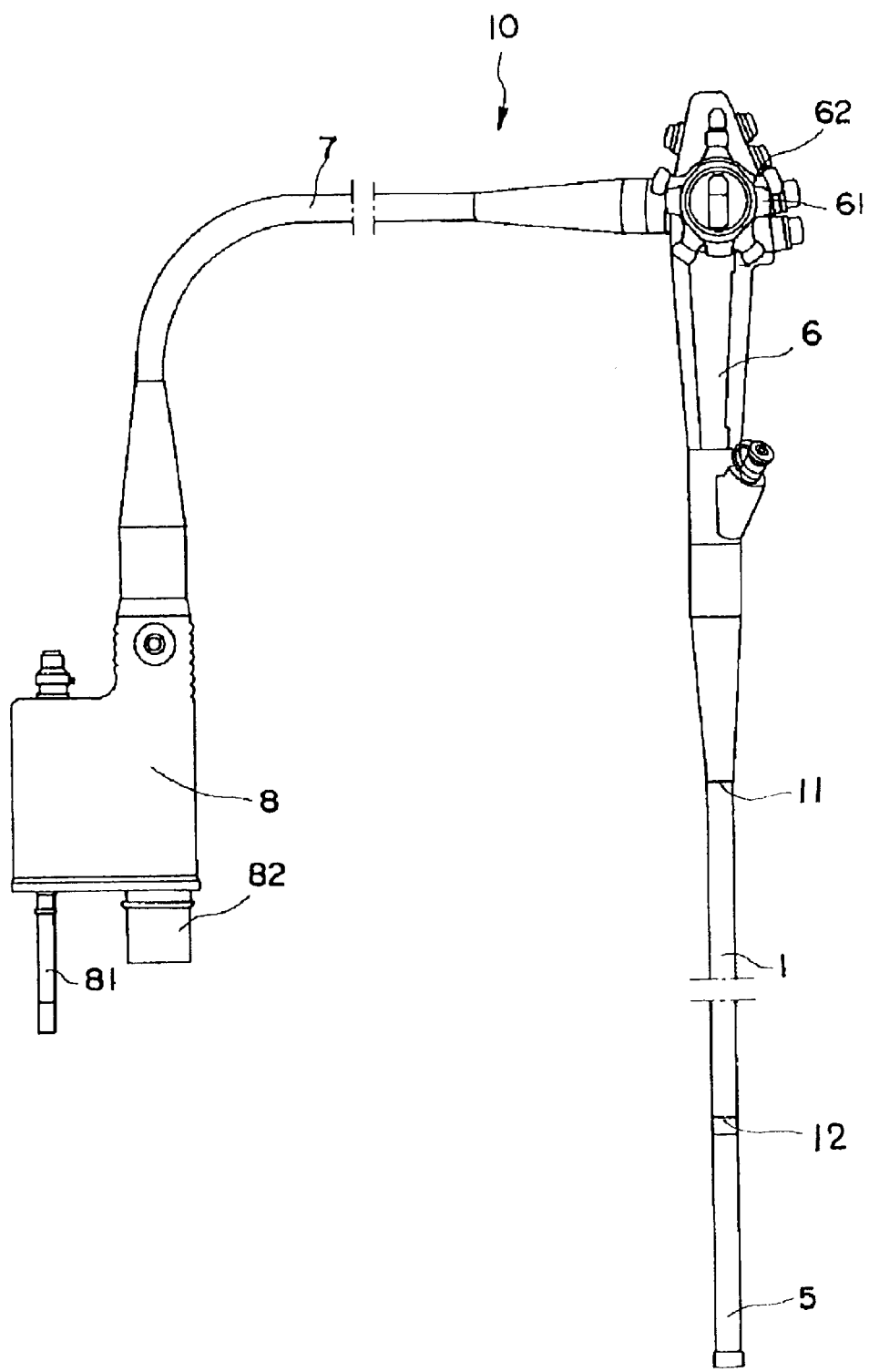
FIG. 1 is an overall view showing an electronic endoscope having a flexible tube constructed in accordance with the present invention.

FIG. 1 is an overall view showing an electronic endoscope having a flexible tube constructed in accordance with the present invention. In the following description, the upper side and the lower side in FIG. 1 will be referred to as "base or proximal end" and "tip or distal end," respectively.

As shown in FIG. 1, the electronic endoscope 10 includes an elongated flexible tube (insertion section) 1 to be inserted into a body cavity of a living body; a bendable tube 5 provided on the tip end 12 of the flexible tube 1; an operating section 6 provided on the base end 11 of the flexible tube 1, which is gripped by an operator during an endoscopic examination to manipulate the endoscope 10; a light guide flexible tube 7 connected at one end thereof to the operating section 6; and a light source plug section 8 provided on the other end of the light guide flexible tube 7 for connection with a light source device (not shown in the drawings).

On the side faces of the operating section 6, there are provided operating knobs 61 and 62. When changing the direction of the bendable tube 5 during the endoscopic examination, the operator turns each of the operating knobs 61 and 62 to pull appropriately wires (not shown) arranged in the flexible tube 1. In this way, the bendable tube 5 is bent to a desired direction.

An imaging element (CCD) not shown in the drawings is provided in the tip end portion of the bendable tube 5 to take observation images of an observation region inside the body cavity. Further, an image signal connector 82 is provided at the tip end portion of the light source plug section 8. The image signal connector 82 is connected to the light source device which is connected to a monitor (not shown in the drawing) via a cable.

Further, a light source connector 81 is provided at the tip end portion of the light source plug section 8, and this light source connector 81 is connected to the light source device. Light emitted from the light source device passes through the light source connector 81 and a light guide (not shown in the drawings) comprised of an optical fiber bundle that runs inside the light source plug section 8, the light guide flexible tube 7, the operating section 6, the flexible tube 1 and the bendable tube 5, and then the light is irradiated from the tip end portion of the bendable tube 5 toward the observation region for illumination.

The reflected light from the observation region (which forms an image of the observation region) is received by the imaging element. Then, the imaging element outputs an image signal corresponding to the image formed on the imaging element by the reflected light. The image signal is transmitted to the light source plug section 8 via an image signal cable (not shown in the drawing) which extends inside the bendable tube 5, the flexible tube 1, the operating section 6 and the light guide flexible tube 7. Then, in the light source device, the image signal is subjected to predetermined processing (such as signal processing, image processing, and the like), and then the processed signal is sent to the monitor. In this way, an image (electronic image) taken by the imaging element is displayed on the screen of the monitor in the form of a motion picture.

In the above, the description was given for the case where the flexible tube for an endoscope according to the present invention is applied to an electronic endoscope (electronic type endoscope). However, it is to be noted that the flexible tube of this invention may also be applied to a fiberscope (optical type endoscope).

Figure 2:
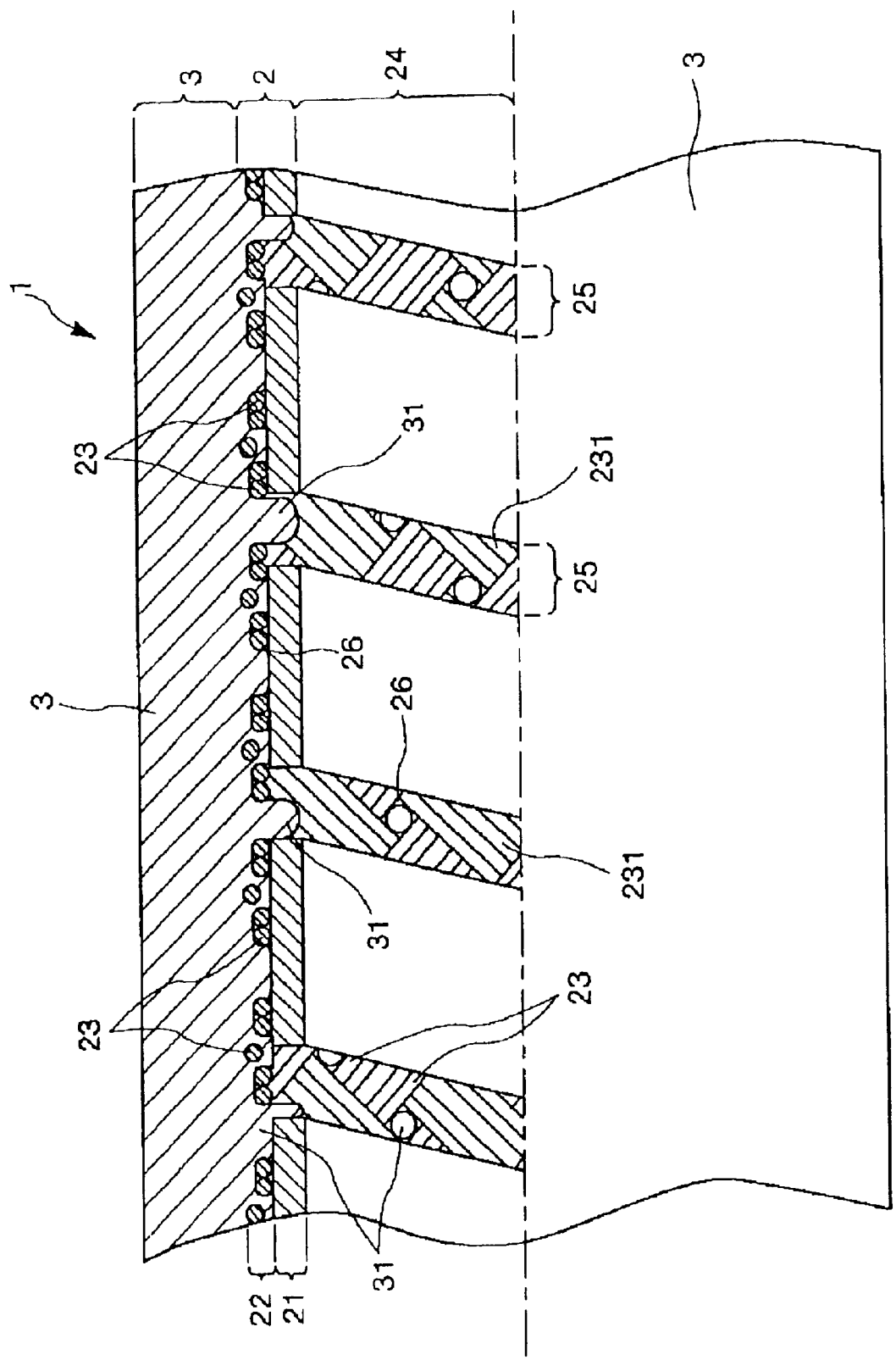
FIG. 2 is a partially cross-sectional view of a portion of a flexible tube for an endoscope of a first embodiment according to the present invention.

FIG. 2 is a partially cross-sectional view of a portion of a flexible tube for an endoscope of a first embodiment according to the present invention.

As shown in FIG. 2, the flexible tube 1 has a core body 2 and an outer cover 3 that covers the outer periphery of the core body 2. Further, inside the flexible tube 1, there is formed hollow spaces 24 through which internal elements (such as optical fibers, cables, operation wires, tubular elements, and the like) can be passed.

The core body 2 acts as a reinforcing member for reinforcing the flexible tube 1, and also acts as a protecting member for protecting the internal elements described above. This core body 2 is formed into an elongated tubular shape, and it is constructed from a helical coil 21 and a reticular tube 22 which covers the outer periphery of the helical coil 21. By constructing the core body 2 from the coil 21 and the reticular tube 22 described above, it becomes possible to give the flexible tube 1 sufficient mechanical strength.

The coil 21 is formed from a flat metal band. Specifically, this coil 21 is formed by winding the metal band into a helical or spiral form so as to have a uniform diameter with a gap 25 between the adjacent windings. Preferred examples of materials which may be used for the metal band include stainless steel, copper alloys, and the like.

Figure 3:
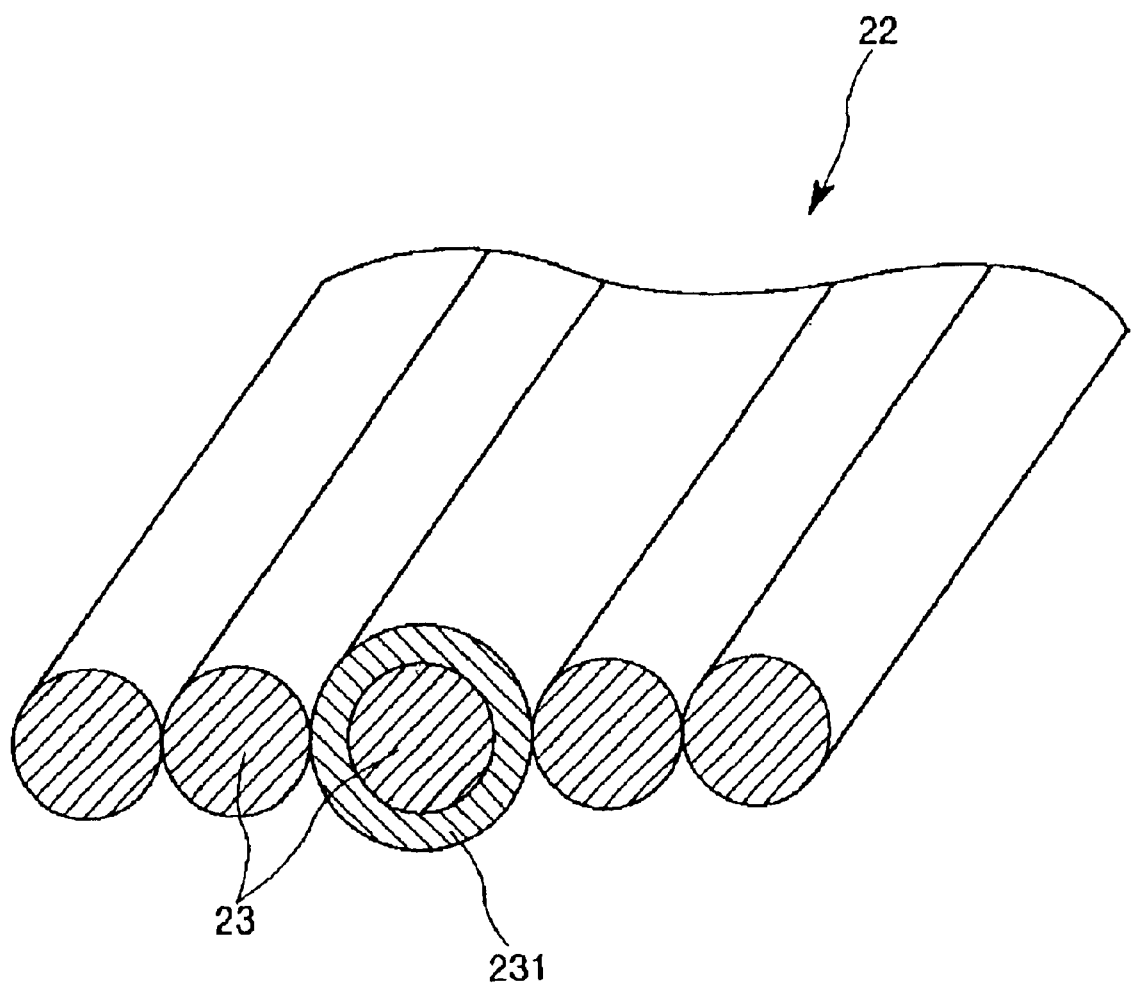
FIG. 3 is an enlarged cross sectional view of a reticular tube which is used in the flexible tube for an endoscope of the present invention.
Figure 4:
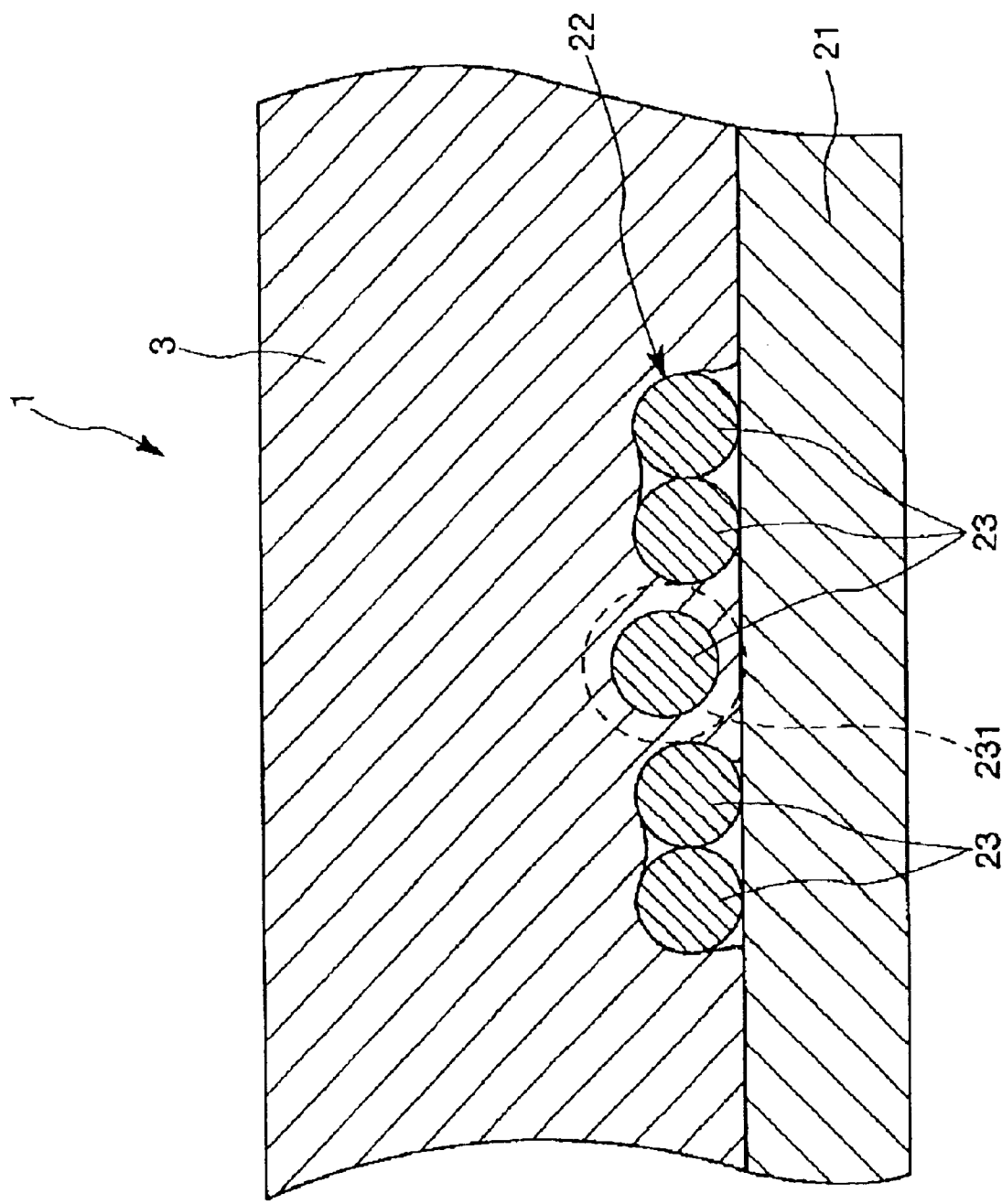
FIG. 4 is an enlarged cross sectional view which shows the structure of a portion in the vicinity of the reticular tube of the flexible tube shown in FIG. 2.

FIG. 3 is an enlarged cross-sectional view of a reticular tube which is used for the flexible tube for an endoscope of the present invention. FIG. 4 is an enlarged cross sectional view which shows the structure of a portion in the vicinity of the reticular tube of the flexible tube shown in FIG. 2.

The reticular tube (braided member) 22 is formed by braiding a plurality of metals or nonmetal fine wires 23 into a tubular lattice structure. Examples of the metallic material which can be used for the fine wires 23 include iron alloy such as stainless steel, copper alloy, and the like. Further, examples of the nonmetallic material which can be used for the fine wires 23 include resins having a high melting point, carbon fibers, glass fibers, and the like.

Further, as shown in FIG. 3, there is formed a coating layer 231 over at least one of the fine wires 23. The coating layer 231 is constituted from a material which includes the constituent material of the outer cover 3 (that is, the constituent material of at least a portion of the outer cover 3 facing the reticular tube 22) as described later in detail. In this regard, it should be noted that the constituent material means the main material of the outer cover, and does not include additives and the like. By providing such a coating layer 231, it becomes possible to strongly bond (fuse together) the coating layer 231 and the outer cover 3, as shown in FIG. 4. As a result, the adhesion (bonding strength) between the reticular tube 22 and the outer cover 3 is enhanced, so that the resilience and durability of the flexible tube 1 are improved.

Normally, the material used for the constituent material of the outer cover 3 is chosen in view of its cushioning ability (flexibility). Therefore, if the ratio of the constituent material of the outer cover 3 used in the constituent material of the coating layer 231 is too large, the coating layer 231 will have a high viscosity. As a result, when braiding the fine wire 23 covered with the coating layer 231, such braiding operation will become difficult due to the high viscosity, thus leading to the case that the reticular tube 22 has an uneven surface. On the other hand, if the ratio of the constituent material of the outer cover 3 used in the constituent material of the coating layer 231 is too small, a sufficient adhesion (bonding strength) between the coating layer 231 and the outer cover 3 will not be obtained, which results in the case that the effect of the present invention is not sufficiently obtained. Accordingly, the ratio of the constituent material of the outer cover 3 used in the constituent material of the coating layer 231 should preferably be in the range of 5–80 wt %, more preferably in the range of 7–60 wt %, and even more preferably in the range of 10–50 wt %.

The outer cover 3 described above is usually formed by extrusion molding the constituent material of the outer cover 3 over the outer periphery of the core body 2 (i.e., the outer periphery of the reticular tube 22). In the case where the outer cover 3 is formed in this manner, the constituent material of the outer cover 3 needs to be sufficiently melted or softened in order to accomplish a good coating that does not form any unevenness or roughness.

However, in the case where the outer cover 3 is formed using such a constituent material, there is a case that the following problem will arise. Namely, if the melting point of the constituent material of the coating layer 231 is below the melting point of the constituent material of the outer cover 3, there is a risk that the coating layer 231 is melted when the outer cover 3 is formed and thereby the adhesion of the fine wire 23 and the coating layer 231 is lowered. In order to avoid such an unfavorable situation, in the present invention, when the constituent material of the coating layer 231 has a melting point $T_1$ (° C.), and the constituent material of the outer cover 3 has a melting point $T_2$ (° C.), the relationship $T_1 > T_2$ needs to be satisfied. In this case, it is particularly preferred that the difference between the melting point ($T_1$) of the constituent material of the coating layer 231 and the melting point ($T_2$) of the constituent material of the outer cover 3 lies within the range of 4–200° C., and more preferably in the range of 4–70° C. If the melting points $T_1$ and $T_2$ satisfy this relationship, it is possible to obtain good adhesion between the fine wire 23 and the coating layer 231 as well as good adhesion between the reticular tube 22 and the outer cover 3.

In this connection, it is preferred that the melting point $T_1$ of the constituent material of the coating layer 231 is in the range of 120–350° C., and more preferably in the range of 180–330° C., for example.

The constituent material of the coating layer 231 is not particularly limited to a specific material. For example, it is possible to use various resins having flexibility such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and one of various elastomers such as polyurethane-based elastomer, polyester-based elastomer, polyolefin-based elastomer, polyamide-based elastomer, silicone rubber, latex rubber, and the like; and blended body, copolymer(including block copolymer) or polymer alloy each having at least one of these materials as a main ingredient. In this case, a mixture of one or two or more kinds of these materials may be employed.

Among these materials, a material containing polyamide-based resin is particularly preferred. When such a material containing the polyamide-based resin is used as the constituent material of the coating layer 231, it is possible to obtain excellent adhesion between the coating layer 231 and the fine wire 23 as well as excellent adhesion between the coating layer 231 and the outer cover 3. This means that the adhesion between the reticular tube 22 and the outer cover 3 is also improved, and as a result, the flexible tube 1 will have excellent resilience and durability.

Further, it is also preferred that the constituent material of the coating layer 231 contains polyurethane-based elastomer. When such a material containing the polyurethane-based elastomer is employed as the constituent material of the coating layer 231, it is also possible to obtain excellent adhesion between the outer cover 3 and the coating layer 231 and it is also possible for the flexible tube 1 to have excellent flexibility in the case where the constituent material of the outer cover 3 is polyurethane-based elastomer (in particular, a material containing polyurethane-based elastomer as its main ingredient).

The average molecular weight (Mw) of the constituent material of the coating layer 231 is not particularly limited, but it should preferably lie within the range of 10000–8000000, and more preferably within the range of 15000–100000, for example.

When necessary, additives may be added in the constituent material of the coating layer 231.

Examples of the additives include plasticizer; inorganic filler; pigment; various kinds of stabilizers (antioxidant, photo stabilizer, antistatic agent, blocking inhibitor, lubricant); X-ray contrast medium, and the like.

The average thickness of the coating layer 231 is not particularly limited to a specific value, but is should preferably lie within the range of 0.01–0.1 mm, more preferably within the range of 0.02–0.08 mm, and even more preferably within the range 0.03–0.05 mm, for example. If the average thickness of the coating layer 231 is lower than the lower limit value, there is a possibility that the effect of the present invention is not sufficiently obtained. On the other hand, if the average thickness of the coating layer 231 exceeds the above upper limit, there is a case that the surface of the flexible tube 1 becomes rough or uneven, thus leading to poor appearance.

The reticular tube (braided member) 22 has many spaces due to the stitches of the braided fine wires 23. These spaces 26 become concave portions at the positions that overlap with the outer periphery of the coil 21, and become holes extending to the hollow spaces 24 at the positions which overlap with the gaps 25 of the coil 21. Therefore, a plurality of holes and concave portions are formed in the outer periphery of the core body 2.

Since the outer periphery of the core body 2 is covered with the flexible outer cover 3, a plurality of protruding portions (anchors) 31 which protrude toward the inside are formed on the inner peripheral surface of the outer cover 3 so as to be integral portions that extend into the spaces from the outer cover 3. Specifically, these protruding portions 31 extend into the plurality of holes and concave portions formed in the outer periphery of the core body 2. The tips of the protruding portions 31 that protrude into the concave portions are formed so as to reach the outer periphery of the coil 21. The protruding portions 31 that protrude into the holes are formed to be even longer in order for the tips thereof to extend into the gaps 25 of the coil 21.

As described above, the protruding portions 31 engage with the plurality of holes and concave portions formed in the outer periphery of the core body 2. Therefore, an anchor effect will occur, and this will reliably secure the outer cover 3 to the core body 2. As a result, even in the case where the flexible tube 1 is bent, the outer cover 3 will maintain a bonded state with the core body 2, and will undergo large expansion and contraction to follow the bending of the core body 2. Further, the restoring force of the outer cover 3 undergoing such large expansion and contraction is strong enough to serve as a force for restoring the shape of the bent flexible tube 1. Accordingly, by adopting such structure as described above, the flexible tube 1 can have excellent resilience.

Further, due to the protruding portions 31 described above, the outer cover 3 is firmly bonded with the reticular tube 22, so that the outer cover 3 will be difficult to peel off from the reticular tube 22 even over repeated use. Accordingly, because the flexible tube 1 will maintain excellent resilience even after repeated use, the flexible tube 1 will have excellent durability.

Furthermore, the formation of the protruding portions 31 described above provide a synergistic effect in combination with the anchoring effect and the effect resulted from the provision of the coating layer 231 described above, so that the flexible tube 1 can have especially excellent resilience and durability.

The melting point $T_2$ of the constituent material of the outer cover 3 varies depending on the type of constituent material to be used in the coating layer 231. Preferably, the melting point $T_2$ is in the range of 120–310°C., and more preferably in the range of 170–220° C. In this regard, it should be noted that the melting point $T_2$ of the constituent material of the outer cover 3 satisfies the relationship of T1>T2 described above.

The constituent material of the outer cover 3 is not particularly limited to a specific material. It is possible to use various resins having flexibility such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefin-based elastomer, polyamide-based elastomer, silicone rubber, latex rubber, and the like; and blended body, copolymer(including block copolymer) or polymer alloy each having at least one of these materials as a main ingredient. In this case, a mixture of one or two or more kinds of these materials may be employed. Among these materials, a material containing polyurethane-based elastomer is preferred, and a material containing polyurethane-based elastomer as its main ingredient is particularly preferred. By forming the outer cover 3 from such a material, it is possible to obtain a flexible tube 1 having excellent flexibility. Examples of the urethane-based elastomer include ether-based, ester-based, caprolactam-based, and polycarbonicacid-based, and the like.

The average molecular weight (Mw) of the constituent material of the outer cover 3 is also not particularly limited to a specific value. However, it is preferable that the average molecular weight is in the range of 10000–8000000, and more preferably in the range of 15000–100000.

When necessary, additives may be added in the constituent material of the outer cover 3.

Examples of the additives include plasticizer; inorganic filler; pigment; various kinds of stabilizers (antioxidant, photo stabilizer, antistatic agent, blocking inhibitor, lubricant); X-ray contrast medium, and the like.

A description of the constituent material of the outer cover 3 was given above. In this regard, it should be noted that the components (i.e., the composition ratio of ingredient) of the constituent material of the outer cover 3 may be uniformly distributed throughout the entire outer cover 3, or the components may be distributed at different ratios at each portion thereof. For example, the contents of the constituents may be gradually changed in the thickness direction thereof (that is, graded materials may be used).

Further, it is sufficient in this invention that the constituent material of the coating layer 231 is included in at least a portion of the outer cover 3 that faces the reticular tube 22 (near the inner surface of the outer cover 3).

Further, it is preferred that the outer cover 3 (excluding those portions that have the protruding portions 4) has a substantially uniform thickness along the longitudinal direction thereof. This structure further improves the operability when the flexible insertion tube 1 is inserted into a body cavity, and thereby the burden placed on the patient can be further reduced.

In this regard, so long as the core body 2 and the instruments passed through the inside thereof are protected from body fluids and the like, and so long as the bendability of the flexible tube 1 is not impaired, there is no specific limitation on the average thickness of the outer cover 3

(excluding those portions that have the protruding portions 4), but normally the average thickness should preferably in the range of 0.01–1.5 mm, more preferably in the range of 0.05 –1 mm, and even more preferably in the range of 0.1–0.8 mm.

An example of a manufacturing method for manufacturing the flexible insertion tube 1 will now be described.

First, the helical coil 21 and the reticular tube 22 are prepared.

The coil 21 is formed, for example, by preparing a metal plate, and then subjecting such a metal plate to a shearing process and then a winding process.

Further, the reticular tube 22 is formed by braiding fine wires 23. In this regard, it is preferred that before the fine wires 23 are braided, the coating layer 231 is in advance formed on at least one of the fine wires 23.

The constituent material of the coating layer 231 is obtained, for example, by melting or softening each of the components described above, and then mixing and kneading such components together. In order to carry out such mixing and kneading of the melted or softened components, it is possible to use a kneading machine or the like such as a kneader, a kneading rooter, rollers, a continuous kneading extrusion machine or the like. In the case where such a kneading machine is used to knead the components together, the material will have a uniform mixture of each of the components.

As for the kneading temperature, there are no specific restrictions, but the temperature should preferably in the range of 140–360° C., more preferably in the range of 160–340° C., and even more preferably in the range of 180–320° C. In the case where each component is kneaded at a temperature within this range, it is possible to improve the uniformity of the components in the material.

However, in the case where the main component of the constituent material of the coating layer 231 is a rubber compound such as silicone rubber or the like, the heat generated during such kneading will degrade the plasticity of the constituent material of the coating layer 231. Accordingly, in this case, the kneading is preferably carried out at a temperature within the range of 10–70° C.

Then, the material kneaded in such a way is applied over the fine wire 23 by an extrusion molding method, molding method, dipping method, coating method or the like, and in this way it is possible to form the coating layer 231.

Next, the coil 21 and the reticular tube 22 obtained in this way are assembled to form the core body 2.

Then, the outer periphery of the core body 2 is covered with the outer cover 3 to form the flexible tube 1.

The constituent material of the outer cover 3 can be obtained, for example, by melting or softening each of the components described above, and then mixing and kneading such components together. In order to carry out such mixing and kneading of the melted or softened components, it is possible to use a kneading machine or the like such as a kneader, a kneading rooter, rollers, a continuous kneading extrusion machine or the like. In the case where such a kneading machine is used to knead the components together, the material will have a uniform mixture of each of the components.

As for the kneading temperature, there are no specific restrictions, but the temperature should preferably in the range of 160–220° C., more preferably in the range of 180–210° C., and even more preferably in the range of 185–205° C. In the case where each component is kneaded at a temperature within this range, it is possible to improve the uniformity of the components in the material.

However, in the case where the main component of the constituent material of the outer cover 3 is a rubber compound such as silicone rubber or the like, the heat generated during such kneading will degrade the plasticity of the constituent material of the outer cover 3. Accordingly, in this case, the kneading is preferably carried out at a temperature within the range of 10–70° C.

Further, when the outer cover material kneaded in this way is applied over the core body 2 using an extrusion molding method, it is possible to manufacture the flexible tube 1 in a continuous manner.

Preferably, the temperature t of the outer cover material during the extrusion molding is greater than or equal to the melting point ($T_2$) of the constituent material of the outer cover 3, and less than the melting point ($T_1$) of the constituent material of the coating layer 231. In the case where the temperature t of the outer cover material during extrusion molding is within such temperature range (i.e., $T_2 \leq t < T_1$), the material can have excellent moldability and processability when being formed into the outer cover 3, and thereby the adhesion with the coating layer 231 is improved. Further, because the temperature t of the outer cover material is less than the melting point ($T_1$) of the constituent material of the coating layer 231, it is possible to prevent the coating layer 231 from being melted during the extrusion molding process to lower the adhesion between the fine wires 23 and the coating layer 231. Consequently, the adhesion between the reticular tube 22 and the outer cover 3 is improved, and this gives the flexible tube 1 excellent resilience and durability.

Figure 5:
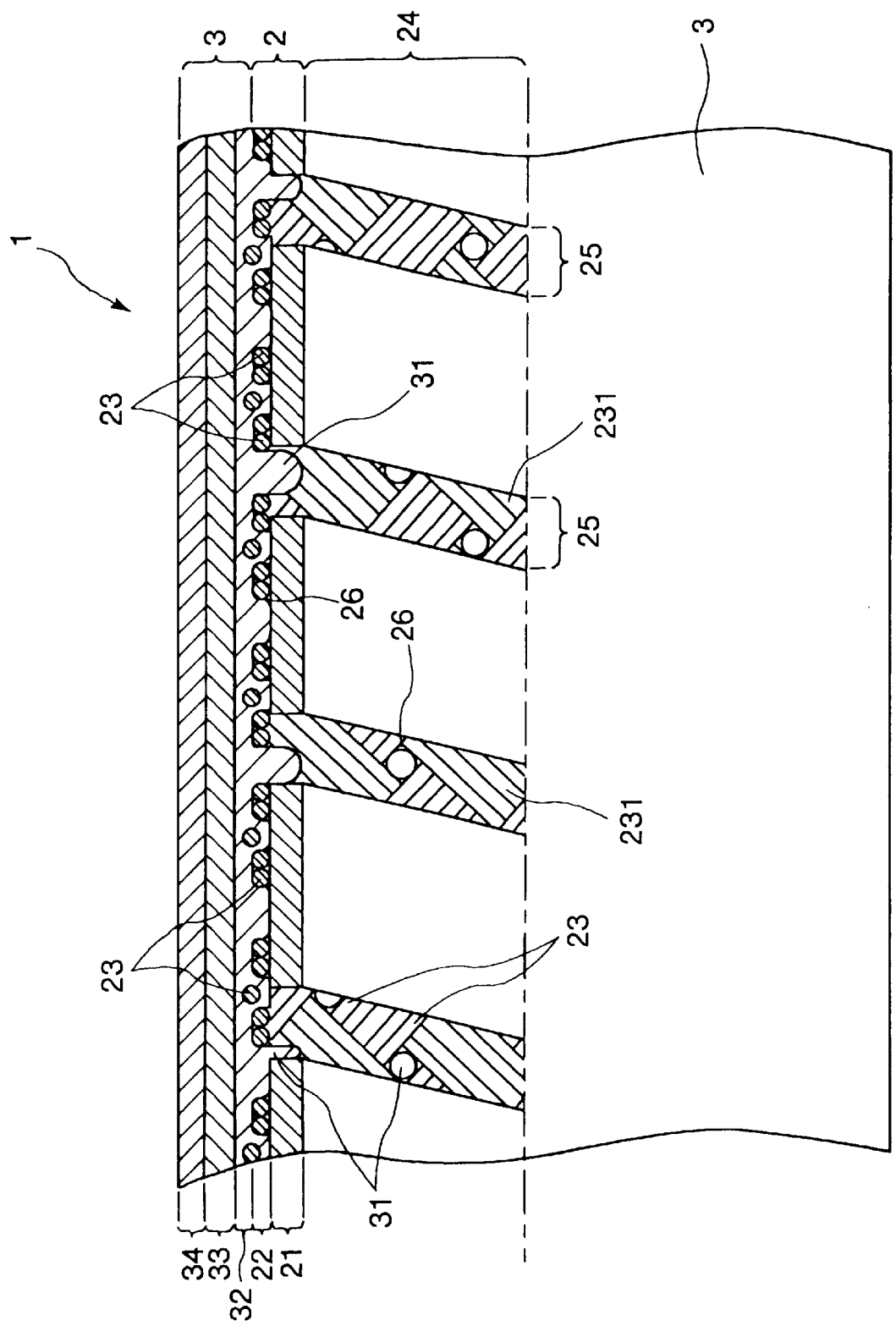
FIG. 5 is a partially cross-sectional view of a portion of a flexible tube for an endoscope of a second embodiment according to the present invention.

Next, FIG. 5 is a partially cross-sectional view of a portion of a flexible tube for an endoscope of a second embodiment according to the present invention. In this regard, the description given below for the flexible tube 1 shown in FIG. 5 will focus on elements that are different from those described above in the first embodiment, and therefore a description of the same elements is omitted.

Namely, in the flexible tube 1 of the second embodiment, the outer cover 3 is formed into a laminated structure which includes an inner layer 32, an intermediate layer 33 and an outer layer 34.

As described below, in this outer cover 3, one of the inner layer 32, the intermediate layer 33 and the outer layer 34 is made of a material having different physical and chemical properties (referred to collectively as the "material properties") than any one of the other layers. Examples of physical properties include stiffness (flexibility), hardness, elongation percentage, tensile strength, shear strength, flexural elasticity, bending strength and the like, and examples of chemical properties include chemical resistance, weather resistance and the like. In this regard, it should be noted that the present invention is not limited to these examples, and it is of course possible to include any other material properties.

The inner layer 32 is formed at the innermost peripheral side of the outer cover 3 so as to make contact with the core body 2. Accordingly, the constituent material of the inner layer 32 is preferably chosen to have excellent adhesion with the core body 2 (in particular, the coating layer 231). Further, the inner layer 32 is preferably formed of a material suited for forming protruding portions 31 having appropriate size (length), shape and number. By forming the inner layer 32 with such a material, it is possible to control the resilience and durability of the flexible tube 1.

Further, the inner layer 32 is preferably formed of the same material used as the constituent material of the outer cover 3 of the first embodiment described above. This means that the inner layer is formed of a material that exhibit excellent adhesion with the coating layer 231 of the reticular tube 22.

The average thickness of the inner layer 32 (excluding those portions that have the protruding portions 31) is not particularly limited to a specific value, but it should preferably be in the range of 0.03–0.8 mm, and more preferably in the range of 0.03–0.4 mm.

The intermediate layer 33 is formed over the outer peripheral surface of the inner layer 32. The intermediate layer 33 is preferably formed as a layer having better resilience than the outer layer 34 described below. According to this structure, the intermediate layer 33 will function as a cushioning layer between the inner layer 32 and the outer layer 34. Further, the intermediate layer 33 is preferably formed as a layer having better flexibility than the inner layer 32.

The cushioning function of the intermediate layer 33 will now be described in detail. Namely, when the flexible tube 1 is bent, the deformed intermediate layer 33 generates a strong restoring force because of the high resilience of the intermediate layer 33. Then, since the intermediate layer 33 is arranged between the outer layer 34 and the inner layer 32 both having relatively high hardness, the restoring force of the intermediate layer 33 is transmitted efficiently to the inner layer 32 and the outer layer 34, respectively. As a result, almost all of the restoring force of the intermediate layer 33 functions as a force for restoring the bent flexible tube 1. Accordingly, by constructing the outer cover 3 with the laminated structure described above, it is possible to obtain a flexible tube having excellent resilience.

The constituent material of the intermediate layer 33 is not particularly limited to a specific material. It is possible to use various resins having flexibility such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefin-based elastomer, polyamide-based elastomer, silicone rubber, latex rubber, and the like; and blended body, copolymer(including block copolymer) or polymer alloy each having at least one of these materials as a main ingredient. In this case, a mixture of one or two or more kinds of these materials may be employed.

Among these materials, low hardness polyurethane-based elastomer, polyolefin-based elastomer, and polyester-based elastomer are particularly preferred because they have excellent resilience.

The average thickness of the intermediate layer 33 is not particularly limited, but it should preferably be in the range of 0.02–0.8 mm, and preferably in range of 0.02–0.4 mm.

The outer layer 34 is formed at the outermost peripheral side of the outer cover 3.

The outer layer 34 is preferably formed of a material having chemical resistance. By forming the outer layer from such a material, the outer cover 3 will suffer very little degradation even over repeated cleaning and sterilization. As a result, there is less possibility that the outer cover 3 is hardened to reduce its flexibility or that the outer cover 3 is peeled off from the reticular tube 22 due to occurrence of crack and the like.

The constituent material of the outer layer 34 is not particularly limited. It is possible to use various resins having flexibility such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefin-based elastomer, polyamide-based elastomer, silicone rubber, latex rubber, and the like; and blended body, copolymer(including block copolymer) or polymer alloy each having at least one of these materials as a main ingredient. In this case, a mixture of one or two or more kinds of these materials may be employed.

Among these materials, polyolefin such as ethylene-vinylacetate copolymer, fluoro-based resin such as polytetrafluoroethylene, ethylene-tetrafluoroethylene copolymer and the like, polyester-based elastomer, polyolefin-based elastomer, fluorine-based elastomer, and silicone rubber are particularly preferred because they have excellent chemical resistance.

The average thickness of the outer layer 34 is not particularly limited, but it should preferably be in the range of 0.05–0.8 mm, and more preferably in the range of 0.05–0.4 mm.

Further, it should be noted that the laminated structure formed by laminating the plurality of layers described above may be used for the entire length of the outer cover 3 or for at least a part thereof.

By constructing the outer cover 3 from the laminated structure having the plurality of layers as described above, it is possible to enjoy the advantages of the respective materials used in each layer. In this embodiment, because the outer cover 3 is constructed from the outer layer 34 having excellent chemical resistance, the intermediate layer 33 having excellent resilience, and the inner layer 32 having excellent adhesion with the core body 2, all of the advantages resulted from these properties are enjoyed in the outer cover 3.

This type of flexible tube can be manufactured in the same manner as was described above for the first embodiment. In particular, in the case where an extrusion molding machine equipped with a plurality of extrusion openings is used, each of the inner layer, intermediate layer and outer layer is respectively extruded through such extrusion openings at the same time, and by covering the core body with such a laminated body, it is possible to continuously manufacture an outer cover having the laminated structure. Further, by adjusting the pulling speed of the core body and the discharge quantity of the constituent material of each layer extruded through each extrusion opening, it is possible to control the thickness of each layer.

In the foregoing, the description was made with regard to the preferred embodiments of the present invention, the present invention is not limited to these specific embodiments described above.

For example, in the second embodiment, instead of the three layered structure including the inner layer 32, the intermediate layer 33 and the outer layer 34, the outer cover 3 can be constructed from just two layers (e.g., the intermediate layer 33 can be omitted, and just the inner layer 32 and the outer layer 34 can be used), or the outer cover 3 can be constructed from four or more layers.

Further, as an alternative method of manufacturing the flexible tube for an endoscope, the following method may be employed. That is, first, the outer cover 3 is formed as a continuous elongated body, and then the core body 2 is inserted into this outer cover 3, whereafter a heating process or the like is carried out to bond the outer cover 3 to the core body 2.

Furthermore, the flexible tube for an endoscope of the present invention can also be applied to flexible connection tubes and the like connected to a light source device.

EXAMPLES

Next, specific examples of the present invention will be described below.

1. Preparation of Flexible Tube for Endoscope

Example 1

First, a coil 21 having an outer diameter of 9.9 mm and an inner diameter of 9.6 mm were prepared by winding a band-shaped stainless steel member having a width of 3 mm.

Next, stainless steel fine wires each having a diameter of 0.1 mm were prepared. Some of these wires were given a coating layer along the entire length thereof, respectively. As the constituent material of the coating layer, a mixture containing 5 wt % of polyurethane-based elastomer (manufactured and sold by DAINIPPON INK AND CHEMICALS Inc. with the product name of PANDEX and the product code of T-1180) and 95 wt % of polyamide-based resin (manufactured and sold by Mitsubishi Engineering-Plastics Corporation with the product name of NOVAMID and the product code of 1010C) was employed. The mixture had a melting point $T_1$ of 220° C. This coating layer was formed using an extrusion molding method. The average thickness of the coating layer was 0.05 mm.

A plurality of bundles each having three fine wires were prepared. Each bundle was comprised of a fine wire which was given the coating layer thereon and two fine wires having no coating layer. These bundles were braided to obtain a reticular tube.

The coil was covered with the reticular tube obtained in this way to form a core body.

Next, the periphery of this core body is covered with an outer cover 3 (having a melting point $T_2$ of 170° C.) made of polyurethane-based elastomer (manufactured and sold by DAINIPPON INK AND CHEMICALS Inc. with the product name of PANDEX and the product code of T-1180) by using the extrusion molding method to obtain a flexible tube for an endoscope with a length of 1.5 m. The temperature (t) of the outer cover material during extrusion molding was 200° C. Further, the average thickness of the outer cover of the flexible tube for an endoscope obtained in this way was 0.3 mm.

Examples 2–9

Flexible tubes for an endoscope were prepared in the same manner as in Example 1 except that the composition ratio between polyurethane-based elastomer and polyamide-based resin was changed as shown in the attached Table 1.

Example 10

A flexible tube for an endoscope was prepared in the same manner as in Example 3 except that the outer cover which covers the core body was formed into a laminated structure (laminated body) which includes an inner layer, an intermediate layer and an outer layer. The laminated body was formed using an extrusion molding machine equipped with three extrusion openings. Specifically, each of the inner layer, intermediate layer and outer layer was extruded at the same time, and by covering the core body with such a laminated body, an outer cover having the laminated structure was continuously manufactured. As the constituent material of each of the inner layer, the intermediate layer and the outer layer, polyurethane-based elastomer (having a melting point of 170° C. and manufactured and sold by DAINIPPON INK AND CHEMICALS Inc. with the product name of PANDEX and the product code of T-1180), polyurethane-based elastomer (manufactured and sold by DAINIPPON INK AND CHEMICALS Inc. with the product name of PANDEX and the product code of T-1498) or polyurethane-based elastomer (manufactured and sold by DAINIPPON INK AND CHEMICALS Inc. with the product name of PANDEX and the product code of T-1495) was employed, respectively.

The average thickness of each of the inner layer, the intermediate layer, and the outer layer was 0.05 mm, 0.1 mm and 0.1 mm, respectively.

Comparative Example 1

A flexible tube for an endoscope was prepared in the same manner as in Example 1 except that no coated layer was formed on the fine wires.

Comparative Example 2

A flexible tube for an endoscope was prepared in the same manner as in Example 1 except that polyamide-based resin (having a melting point of 225° C. and manufactured and sold by Mitsubishi Engineering-Plastics Corporation with the product name of NOVAMID and the product code of 1010C) was employed as the constituent material of the coating layer.

Comparative Example 3

A flexible tube for an endoscope was prepared in the same manner as in Example 1 except that polyurethane-based elastomer (having a melting point of 170° C. and manufactured and sold by DAINIPPON INK AND CHEMICALS Inc. with the product name of PANDEX and the product code of T-1180) as the constituent material of the coating layer.

2. Evaluation of Properties of the Flexible Tubes [2.1] Resilience Test

A resilience test was conducted on each of the flexible tubes manufactured using each of the specific examples and each of the comparative examples.

In the resilience test, both ends of each of the flexible tubes were supported and then it was bend at 90°, and then the resilience at such time was evaluated according to the four rankings given below.

A: Extremely good resilience; most suitable for use as a flexible tube for an endoscope B: Good resilience; suitable for use as a flexible tube for an endoscope C: Slightly poor resilience; questionable in suitability for use as a flexible tube for an endoscope D: Poor resilience; not suitable for use as a flexible tube for an endoscope The results of the resilience test are shown in the attached Table 2.

[2.2] Outer Cover Adhesion Test

An outer cover adhesion test was conducted on each of the flexible tubes manufactured using each of the specific examples and each of the comparative examples.

In the outer cover adhesion test, a U-shaped cut was made into the outer cover of each of the flexible tubes, and then the peel strength required to peel off such cut portion of the outer cover was measured. The measurement of such peeling strength was carried out using a digital force gauge, and the peeling angle was 30° with respect to the axial direction of the flexible tube. When the peeling strength of the outer cover of the flexible tube for an endoscope in the case where no coating layer (i.e., the coating layer 231) was formed (i.e., the case of Comparative Example 1) was assigned the value "1", the relative peeling strengths of the outer covers of the flexible tubes were measured, respectively. The results of the measurements are shown in the attached Table 2.

[2.3] Durability Test

A durability test was conducted on each of the flexible tubes manufactured using each of the specific examples and each of the comparative examples.

In the durability test, both ends of each of the flexible tubes were supported, and a 90° bending operation was repeated 300 times, whereafter the same resilience test described above was carried out to compare the resilience after such repeated bending with the resilience before such repeated bending to evaluate the loss of resilience according to the four rankings given below. In this regard, it is to be noted that the loss of resilience is considered to be resulted from peeling off of the internal portion of the outer cover (i.e., the outer cover is peeled off from the core body). Accordingly, the flexible tubes that can maintain their resilience will have excellent durability.

A: Virtually no change in resilience; extremely good durability

B: Slight loss of resilience; good durability

C: Noticeable loss of resilience; questionable in its durability

D: Significant loss of resilience; degradation was confirmed at various positions The results of the durability test are also shown in the attached Table 2.

As is clear from Table 2, all of the obtained flexible tubes of the specific examples 1–10 (according to the present invention) had good resilience. Further, the flexible tubes of the specific examples 1–10 had excellent outer cover peeling strength and durability. In particular, even though the outer cover of the flexible tube of the specific example 10 had an average thickness (that is, the average thickness of the three layers thereof) that was thinner than that for Specific Examples 1–9, the outer cover peeling strength and durability was roughly the same. In contrast with this, the outer cover peeling strength and durability of the flexible tubes of the comparative examples were noticeably inferior.

As described above, by forming a coating layer (i.e., the coating layer 231) on at least one of the fine wires, the present invention makes it possible to improve the adhesion between the reticular tube (fine wires) and the outer cover. As a result, the present invention makes it possible to obtain a flexible tube for an endoscope having excellent resilience and durability.

Further, in the case where the outer cover is formed into a laminated structure formed by laminating a plurality of layers, it is possible to obtain sufficient resilience and durability with an outer cover having a thinner thickness than that used in the case of a single layer outer cover. Accordingly, the provision of such laminated outer cover makes it possible to reduce the diameter of the flexible tube for an endoscope. Further, by selecting the proper material and thickness for each layer and combining these layers appropriately, it is possible to obtain an additional synergistic effect by the provisions of these layers. With this result, it becomes possible to obtain a flexible tube for an endoscope having excellent properties.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2000-264075 (filed on Aug. 31, 2000) which is expressly incorporated herein by reference in its entirety.

TABLE 1

| | Constituent Material | | | |
|---|---|---|---|---|
| | Content of polyurethane-based elastomer (wt %) | Content of polyamide-based elastomer (wt %) | Melting point $T_1$ (° C.) | Temperature of material of outer cover at extrusion molding (° C.) |
| Example 1 | 5 | 95 | 220 | 200 |
| Example 2 | 10 | 90 | 218 | 200 |
| Example 3 | 20 | 80 | 216 | 200 |
| Example 4 | 30 | 70 | 214 | 200 |
| Example 5 | 40 | 60 | 212 | 200 |
| Example 6 | 50 | 50 | 210 | 200 |
| Example 7 | 60 | 40 | 208 | 200 |
| Example 8 | 70 | 30 | 206 | 200 |
| Example 9 | 80 | 20 | 204 | 200 |
| Example 10 | 20 | 80 | 216 | 200 |
| Comp. Ex. 1 | — | — | — | 200 |
| Comp. Ex. 2 | 0 | 100 | 225 | 200 |
| Comp. Ex. 3 | 100 | 0 | 170 | 200 |

TABLE 2

| | Test for Resiliencet | Peeling Strength of Outer Cover (Relative Strength) | Test for Durability |
|---|---|---|---|
| Example 1 | A | 1.8 | B |
| Example 2 | A | 1.9 | A |
| Example 3 | A | 2.0 | A |
| Example 4 | A | 2.1 | A |
| Example 5 | A | 2.0 | A |
| Example 6 | A | 1.9 | A |
| Example 7 | A | 1.8 | A |
| Example 8 | A | 1.7 | A |
| Example 9 | A | 1.6 | B |
| Example 10 | A | 2.0 | A |
| Comp. Ex. 1 | B | 1 | D |
| Comp. Ex. 2 | B | 1.3 | D |
| Comp. Ex. 3 | B | 1.2 | D |

What is claimed is:

1. A flexible tube for an endoscope, comprising:
an elongated core body composed of a helical coil which is formed by helically winding a flat band member and a braided member formed by braiding thin wires and disposed over the coil; and
a flexible outer cover for covering the core body,
wherein at least one of the thin wires has a coating layer and the flexible outer cover has a portion which is in contact with the coating layer of the thin wire of the braided member, in which the coating layer is formed of a material containing the material of the portion of the outer cover and the material of the coating layer has a higher melting point than that of the material of the portion of the outer cover.

2. The flexible tube for an endoscope as claimed in claim 1, wherein the coating layer contains the material of the portion of the outer cover in the amount of 5 to 80 wt % thereof.

3. The flexible tube for an endoscope as claimed in claim 1, wherein the outer cover is formed of a material containing polyurethane elastomer.

4. The flexible tube for an endoscope as claimed in claim 1, wherein the coating layer is formed of a material containing polyurethane elastomer.

5. The flexible tube for an endoscope as claimed in claim 1, wherein the coating layer is formed of a material containing polyamide based resin.

6. The flexible tube for an endoscope as claimed in claim 1, wherein the difference between the melting point of the material of the coating layer and the melting point of the material of the portion of the outer cover is in the range of 4 to 200° C.

7. The flexible tube for an endoscope as claimed in claim 1, wherein the average thickness of the coating layer is in the range of 0.01 to 0.1 mm.

8. The flexible tube for an endoscope as claimed in claim 1, wherein the average thickness of the outer cover is in the range of 0.01 to 1.5 mm.

9. The flexible tube for an endoscope as claimed in claim 1, wherein the outer cover is formed by extrusion molding.

10. The flexible tube for an endoscope as claimed in claim 1, wherein the outer cover is formed into a laminated structure including an inner layer, an intermediate layer and an outer layer, and the inner layer is formed of a material that exhibits adhesion with the coated layer.

11. An electronic endoscope, comprising:

an operation section which is operated by an operator; and a flexible tube having a proximal end connected to the operation section at the proximal end thereof, the flexible tube including an elongated tubular core composed of a helical coil which is formed by helically winding a flat band member and provided over the coil and a braided member formed by braiding thin wires and an a flexible outer cover formed of a synthetic resin and provided over the outer periphery of the tubular core, wherein at least one of the thin wires has a coating layer and the flexible outer cover has a portion which is in contact with the coating layer of the thin wire of the braided member, in which the coating layer is formed of a material containing the material of the portion of the outer cover and the material of the coating layer has a higher melting point than that of the material of the portion of the outer cover.

12. The electronic endoscope as claimed in claim 11, wherein the outer cover is formed into a laminated structure including an inner layer, an intermediate layer and an outer layer, and the inner layer is formed of a material that exhibits adhesion with the coated layer.

* * * * *